(12) United States Patent
Ren et al.

(10) Patent No.: US 8,835,984 B2
(45) Date of Patent: Sep. 16, 2014

(54) SENSORS USING HIGH ELECTRON MOBILITY TRANSISTORS

(75) Inventors: Fan Ren, Gainesville, FL (US); Stephen John Pearton, Gainesville, FL (US); Tanmay Lele, Gainesville, FL (US); Hung-Ta Wang, Berkeley, CA (US); Byoung-Sam Kang, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 537 days.

(21) Appl. No.: 12/992,002

(22) PCT Filed: Mar. 20, 2009

(86) PCT No.: PCT/US2009/037767
§ 371 (c)(1),
(2), (4) Date: Nov. 10, 2010

(87) PCT Pub. No.: WO2009/151705
PCT Pub. Date: Dec. 17, 2009

(65) Prior Publication Data
US 2011/0068372 A1   Mar. 24, 2011

Related U.S. Application Data (63) Continuation-in-part of application No. PCT/US2008/076885, filed on Sep. 18, 2008.

(60) Provisional application No. 60/975,907, filed on Sep. 28, 2007, provisional application No. 60/973,302, filed on Sep. 18, 2007, provisional application No. 60/982,310, filed on Oct. 24, 2007, provisional application No. 61/060,327, filed on Jun. 10, 2008.

(51) Int. Cl.
*H01L 29/72* (2006.01)
*G01N 27/414* (2006.01)

(52) U.S. Cl.
CPC .................................. *G01N 27/414* (2013.01)
USPC .................................. 257/194; 257/E29.246

(58) Field of Classification Search
CPC .................................................. H01L 29/7787
USPC .......................................... 257/197, E29.246
See application file for complete search history.

(56) References Cited

U.S. PATENT DOCUMENTS

| | | |
|---|---|---|
| 4,734,750 A | 3/1988 | Okamura et al. |
| 4,816,118 A | 3/1989 | Oyama et al. |

(Continued)

FOREIGN PATENT DOCUMENTS

JP   58-167951   4/1983

OTHER PUBLICATIONS

Kang, B.S. at al., "Prostate specific antigen detection using AlGaN/GaN high electron mobility transistors," Applied Physics Letters, Sep. 2007, vol. 91, pp. 112106-1 through 112106-3.

(Continued)

*Primary Examiner* — Edward Wojciechowicz
(74) *Attorney, Agent, or Firm* — Saliwanchik, Lloyd & Eisenschenk (57) ABSTRACT

Embodiments of the invention include sensors comprising AlGaAs/GaAs high electron mobility transistors (HEMTs), inGaP/GaAs HEMTs, InAlAs/InGaAs HEMTs, AlGaAs/InGaAs PHEMTs, InAlAs/InGaAs PHEMTs, Sb based HEMTs, or InAs based HEMTs, the HEMTs having functionalization at a gate surface with target receptors. The target receptors allow sensitivity to targets (or substrates) for detecting breast cancer, prostate cancer, kidney injury, chloride, glucose, metals or pEI where a signal is generated by the HEMI when a solution is contacted with the sensor. The solution can be blood, saliva, urine, breath condensate, or any solution suspected of containing any specific analyte for the sensor.

19 Claims, 5 Drawing Sheets

(56) References Cited

U.S. PATENT DOCUMENTS

| | | | |
|---|---|---|---|
| 5,368,707 | A | 11/1994 | Henkens et al. |
| 6,338,968 | B1 | 1/2002 | Hefti |
| 6,368,795 | B1 | 4/2002 | Hefti |
| 6,485,905 | B2 | 11/2002 | Hefti |
| 6,534,801 | B2 | 3/2003 | Yoshida |
| 2004/0014158 | A1* | 1/2004 | Bacher et al. ............... 435/8 |
| 2005/0263790 | A1 | 12/2005 | Moon et al. |
| 2007/0194225 | A1* | 8/2007 | Zorn ............................. 250/306 |
| 2007/0224128 | A1* | 9/2007 | Dennis et al. ............... 424/10.1 |
| 2012/0267693 | A1* | 10/2012 | Holm-Kennedy ............ 257/253 |

OTHER PUBLICATIONS

Tsai, M.-K. at al., "Depeltion-mode and enhancement-mode AlGaP/GaAs delta HEMTs for low supply-voltage applications," Semiconductor Science and Technology, Jan. 2002, vol. 17, pp. 156-160.

Kwon, Youngwoo et al., "Striped-Channel InAlAs/InGaAs HEMTs with shallow-grating structures," IEEE Transactions on Electrical Devices, Dec. 1996, vol. 43, pp. 2046-2052.

S.C. Hung et al., "Detection of chloride ions using an integrated Ag/AgCl electrode with AlGaN/GaN high electron mobility transistors," May 14, 2008, Applied Physics Letters, 92, 193903.

Yen-Sheng Lu et al. "Anion detection using ultrathin InN ion selective field effect transistors," May 27, 2008, Applied Physics Letters 92, 212102.

S.C. Hung et al., "Integration of Selective Area Anodized AgCl Thin Film with AlGaN/GaN HEMTs for Chloride Ion Detection," Jun. 18, 2008, Electrochemical and Solid-State Letters, 11 (9) H241-H244.

R. Grundbacher et al., "AlGaAs/InGaAs PHEMTs With Asymmetrically Recessed Gates Achieved Through a Four Layer Resist Process," Dec. 1997, Brazilian Journal of Physics, vol. 27/A, No. 4, pp. 130-133.

A. Bouloukou et al., "Novel high-breakdown InGaAs/InAlAs pHEMTs for radio-astronomy applications," 2006, 7th MINT Millimeter-Wave Int. Symp., Finland, pp. 221-226, January.

R. Magno et al., "Low-Power, High-Speed Sb-based HEMTs and HBTs," 2004, The Electrochemical Society, Inc., Abs. 281, 205th Meeting, Jan. 2004.

Steven M. Currie et al., "Proton Tolerance of InAs Based HEMT and DHBT Devices," Jul. 2006, IEEE, Radiation Effects Data Workshop, pp. 66-71.

International Patent Application No. PCT/US2008/076885, Written Opinion of the International Searching Authority and International Search Report, completed May 13, 2009.

Kang, B.S., et al. "Electrical detection of immobilized proteins with ungated AlGaN/GaN high-electron-mobility Transistors," Applied Physics Letters, vol. 87, Issue 023508, Jan. 2005.

Kang, B.S., et al. "Electrical detection of deoxyribonucleic acid hybridization with AlGaN/GaN high electron mobility transistors," Applied Physics Letters, vol. 89, Issue 122102, Jan. 2006.

Kang, B.S., et al. "Electrical detection of biomaterials using AlGaN/GaN high electron mobility transistors," Journal of Applied Physics, vol. 104, Issue 031101, Jan. 2008.

Chen, K.H., et al. "c-erB-2 sensing using AlGaN/GaN high electron mobility transistors for breast cancer detection," Applied Physics Letters, vol. 92, Issue 192103, Jan. 2008.

Wang, H.T., et al. "Electrical detection of kidney injury molecule-1 with AlGaN/GaN high electron mobility transistors," Applied Physics Letters, vol. 91, Issue 222101, Jan. 2007.

Chen, K.H., et al. "Log Hg(II) ion concentration electrical detection with AlGaN/GaN high electron mobility transistors," Sensors and Actuators B 134, pp. 386-389, Jan. 2008.

Wang, H.T., et al. "Fast electrical detection of Hg(II) ions with AlGaN/GaN high electron mobility transistors," Applied Physics Letters, vol. 91, Issue 042114, Jan. 2007.

Wang, H.T., et al. "Selective Detection of Hg(II) Ions from Cu(II) and Pb(II) Using AlGaN/GaN High Electron Mobility Transistors," Electrochemical and Solid-State Letters, vol. 10, Issue 11, Jan. 2007.

Kang, B.S., et al. "pH sensor using AlGaN/GaN high electron mobility transistors with $Sc_2O_3$ in the gate region," Applied Physics Letters, vol. 91, Issue 012110, Jan. 2007.

Kang, B.S., et al. "Role of Gate Oxide in AlGaN/GaN High-Electron-Mobility Transistor pH Sensors," Journal of Electronic Materials, vol. 37, No. 5, Jan. 2008.

Kang, B.S., et al. "Enzymatic glucose detection using ZnO nanorods on the gate region of AlGaN/GaN high electron mobility transistors," Applied Physics Letters, vol. 91, Issue 252103, Jan. 2008.

Chu, B.H., et al. "Enzyme-based lactic acid detection using AlGaN/GaN high electron mobility transistors with ZnO nanorods grown on the gate region," Applied Physics Letters, vol. 93, Issue 042114, Jan. 2008.

U.S. Appl. No. 12/664,022, Claims, filed Dec. 12, 2009.
U.S. Appl. No. 12/997,163, Claims, filed Dec. 9, 2010.
U.S. Appl. No. 12/724,117, Claims, filed Mar. 15, 2010.
U.S. Appl. No. 12/966,531, Claims, filed Dec. 13, 2010.

* cited by examiner

FIG. 7

SENSORS USING HIGH ELECTRON MOBILITY TRANSISTORS

CROSS-REFERENCE TO RELATED APPLICATIONS

The present application is the U.S. national stage application of International Application No. PCT/US2009/037767, filed Mar. 20, 2009, which claims the benefit of U.S. Provisional Application Ser. No. 61/060,327, filed Jun. 10, 2008. International Application No. PCT/US09/037,767 is a continuation-in-part of International Application No. PCT/US2008/076885, filed Sep. 18, 2008, which claims the benefit of U.S. Provisional Application Ser. No. 60/973,302, filed Sep. 18, 2007, U.S. Provisional Application Ser. No. 60/975,907, tiled Sep. 28, 2007, and U.S. Provisional Application Ser. No. 60/982,310, filed Oct. 24, 2007. The applications identified above are hereby incorporated by reference herein in their entirety, including any figures, tables, or drawings.

BACKGROUND OF THE INVENTION

Chemical sensors can be used to analyze a wide variety of environmental and bodily gases, aerosols and fluids for properties of interest.

For example, exhaled breath condensate (EBC) is widely known to be a diagnostically important bodily fluid that can be safely collected. In particular, the breath from deep within the lungs (alveolar gas) is in equilibrium with the blood, and therefore the concentrations of molecules present in the breath is highly correlated with those found in the blood at any given time. Analysis of molecules and pH value in exhaled breath condensate or incondensable gases is a promising method that can provide information on the metabolic state of the human body, including certain signs of cancer, respiratory disease, lungs, intestine, liver and kidney function, and other internal organs. Several different analysis methods including gas chromatography (GC), chemiluminescence, selected ion flow tube (SIFT), and mass spectroscopy (MS) have been used to measure different exhaled biomarkers, including hydrogen peroxide, nitrogen oxide, aldehydes, carbon dioxide, hydrogen, and ammonia. However, these methods show vary significantly in sensitivity.

In another example, chloride ion detection can be accomplished. In the body, chlorine exists primarily as the chloride ion. The chloride ion is an essential mineral for humans, and is maintained to a total body chloride balance in body fluids such as serum, blood, urine, exhaled breath condensate etc., by the kidneys. Chloride can be found in the body mainly in the extracellular fluid along with sodium. Some of body chloride is found inside the cells, with the highest amounts within the red blood cells. As one of the mineral electrolytes, chloride works closely with sodium and water to help the distribution of body fluids. Chloride is easily absorbed from the small intestine. It is eliminated through the kidneys, which can also retain chloride as part of their finely controlled regulation of acid-base balance. Chloride is also found along with sodium in perspiration. Variations in the chloride ion concentration in serum may serve as an index of renal diseases, adrenalism, and pneumonia. Thus, the measurement of this parameter is clinically important. Several analytical methods, such as colorimetry, ion-selective electrodes, activation analysis, X-ray fluorescence spectrometry, and ion chromatography, have been used for the analysis of chlorine in various samples. However, these methods are not portable and require expensive instrumentation. Accordingly, an accurate and fast determination of the inorganic ion content of various aqueous samples at low detection limits is of great interest.

Yet another example of sensing application using body fluid is detecting breast cancer with saliva. The mortality rate in breast cancer patients can be reduced by increasing the frequency of screening. The overwhelming majority of patients are screened for breast cancer by mammography. This procedure involves a high cost to the patient. Moreover, the use of invasive radiation limits the frequency of screening. Recent evidence suggests that salivary testing for markers of breast cancer may be used in conjunction with mammography. Saliva based diagnostics for the protein c-erbB-2, a prognostic breast marker assayed in tissue biopsies of women diagnosed with malignant tumors, has shown tremendous potential. Soluble fragments of the c-erbB-2 oncogene and the cancer antigen 15-3 were found to be significantly higher in the saliva of women who had breast cancer than in those patients with benign tumors. Another recent study concluded that epidermal growth factor (EGF) is a promising marker in saliva for breast cancer detection.

Pilot studies indicate that the saliva test is both sensitive and reliable and is potentially useful in initial detection and follow-up screening for breast cancer. However, currently saliva samples are typically obtained from a patient in a dentist's office then sent to a testing lab; it typically takes a few days to get the test results.

To fully realize the potentials of sensors for environmental, health related, chemical and biomedical applications, technologies are needed that will enable easy, sensitive, and specific detection of chemical or biomolecules at home or elsewhere. It is also desirable that a testing device allows concomitant wireless data transmission into preprogrammed destinations, such as transmitting breast cancer testing results to a doctor or clinic. If inexpensive technologies that can detect and wirelessly transmit testing results for environmental, health related, chemical and biomedical applications can be developed, early diagnosis of cancers or disease can significantly lower mortality and the cost of health care. Real-time wireless remote sensing for chemicals in the environment may reduce the incidence of disasters by alert to a chemical hazard.

BRIEF SUMMARY

Embodiments of the present invention relate to high electron mobility transistors (HEMT) capable of performing sensing applications to detect various molecules, including biomarkers, of interest in different bodily fluid samples. According to embodiments of the present invention, the subject sensors can utilize III-V based HEMTs. For example, the subject sensors can utilize HEMTs such as AlGaN/GaN HEMTs, AlGaAs/GaAs HEMTs, InGaP/GaAs HEMTs, and InAlAs/InGaAs HEMTs. In further examples, the subject sensors can utilize HEMTs such as AlGaAs/InGaAs PHEMTs, InAlAs/InGaAs PHEMTs, Sb based HEMTs, and InAs based HEMTs.

Embodiments of the invention are directed to different surface functionalized HEMT based sensors to detect prostate cancer, breast cancer, markers for acute kidney injury or renal failure, pH, chloride, mercury ions and/or copper ions, arsenic, and glucose, in samples of exhaled breath condensate, saliva, urine, blood, or other fluids. The devices according to embodiments of the invention can also wirelessly transmit results of analysis employing the sensors to facilitate rapid analysis of test results.

One embodiment of the invention is a device for detecting cancer that includes a cancer antibody provided on a gate region of the HEMT. In one specific embodiment, a detector formed via carboxylate succinimdyl ester bound prostate specific antigen (PSA) antibodies linked to thioglycolic acid immobilized on a gold-gated HEMT can be used to detect prostate cancer. In another specific embodiment, a gold-gated HEMT functionalized with a breast cancer antibody can be used as the detector.

One other embodiment is a device for detecting acute kidney injury or renal failure that includes specific antibodies provided on a gate region of the HEMT. In a specific embodiment, the HEMT is functionalized with highly specific KIM-1antibodies through a self-assembled monolayer of thioglycolic acid acts as the detector.

Another embodiment of the invention is a device for detecting changes in pH that includes a dielectric coating on a gate region of the HEMT. For example, an AlGaN/GaN high electron mobility transmitter having a gate dielectric coating such as a thin $Sc_2O_3$ layer can be used as the detector. The device can further include a cooling device to obtain exhaled breath condensates for testing.

Yet another embodiment is a device for detecting chloride that includes a chlorine recognition layer provided on a gate region of the HEMT. In one specific embodiment, Ag/AgCl can be provided on the gate region of the HEMT to detect $Cl^-$ ions. In another specific embodiment, InN can be provided on the gate region of the HEMT to detect $Cl^-$ ions.

Another embodiment of the invention is a device for detection of heavy metals that includes a chelating agent provided on a gate region of the HEMI. In a specific embodiment, a chelating agent can be provided on a gate region of the HEMT. The chelating agent can be, for example, thioglycolic acid ($HSCH_2COOH$), cysteamine ($NH_2CH_2CH_2SH$), 1,2-ethanedithiol ($HSCH_2CH_2SH$), dimercaprol (BAL), diaminoethanetetraacetic acid (EDTA), 2,3-bis-sulfanylbutane-dioic acid (DMSA), or 2,3-dimercapto-1-propanesulfonic acid (DMPS).

Yet another embodiment is a device for detecting glucose in exhaled breath condensate. In a specific embodiment, the device uses an HEMT with a nanorod array selectively grown on the gate area that immobilizes glucose oxidase (GOx). The nanorods may be, for example, metal oxide and nitride based nanorods.

The functionalizing agents, antibodies, and materials can be referred to as target receptors. In the biological arts, the target receptors may also be referred to as substrate receptors.

According embodiments of the disclosed sensors, a portable, low cost, continuous monitor can be provided for environmental and medical applications.

Embodiments of the disclosed sensors can be integrated with a wireless transmitter for monitoring and reporting.

DETAILED DISCLOSURE

Sensor devices according to embodiments of the invention utilize HEMTs incorporating functionalization of the gate surface with detecting receptors. The sensor devices can be used with a variety of solutions having environmental and bodily origins, including saliva, urine, blood, breath (including exhaled breath condensates) and other solutions.

HEMT sensors can be used for detecting gases, ions, pH values, proteins, and DNA with good selectivity by modification of the surface in the gate region of the HEMT. HEMT structures can be used in microwave power amplifiers as well as gas and liquid sensors because of their high 2DEG mobility and saturation velocity.

In one embodiment, the device may include an HEMT that is operably coupled to a thermal electric cooling device, which condenses exhaled breath samples. The thermal water vapor and volatile organic compounds from the exhaled breath condensate change the surface charge on the HEMT to which it is applied, thus changing the current flowing in the HEMT device for a fixed applied bias voltage. In one embodiment, an exhaled breath condensate (EBC) biosensor of the present disclosure can be handheld, low in cost, and capable of real time detection without consumable carrier gases.

Although specific examples of the HEMT for the subject sensor applications have been described as an AlGaN/GaN HEMT, other HEMTs, such as an AlGaAs/GaAs HEMT, an InGaP/GaAs HEMT, or an InAlAs/InGaAs HEMT are used in place of the AlGaN/GaN HEMT for alternative embodiments of the present invention. In further embodiments, the subject sensors can utilize other III-IV based HEMTs such as AlGaAs/InGaAs PHEMTs, InAlAs/InGaAs PHEMTs, Sb based HEMTs, and InAs based HEMTs.

Embodiments of the present invention provide chemically functionalized HEMT devices for target (or substrate) sensing. Specific sensitivity can be achieved by employing a target sensitive layer on the gate area of the HEMT.

The AlGaN/GaN HEMT is an exemplary HEMT that can be used for sensing applications. AlGaN/GaN HEMTs have high electron sheet carrier concentration channel induced by both piezoelectric polarization and spontaneous polarization. Unlike conventional semiconductor field effect transistors, intentional dopant does not need to be included in the AlGaN/GaN HEMT structure. Instead, electrons in the two-dimensional electron gas (2DEG) channel are located at the interface between the AlGaN layer and GaN layer. In addition, there are positive counter charges at the HEMT surface layer induced by the 2DEG. Slight changes in the ambient can affect the surface charge of the HEMT, thus changing the 2DEG concentration in the channel. This operation works similarly in the AlGaAs/GaAs HEMT, InGaP/GaAs HEMT, and InAlAs/InGaAs HEMT (and other HEMTs) at the interface between the dual layer structures (indicated as first material layer/second material layer).

According to embodiments, the 2DEG channel is connected to an Ohmic-type source and drain contacts. The source-drain current is modulated by a third contact, a Schottky-type gate, on the top of the 2DEG channel. For sensing applications, the third contact is affected by the sensing environment, i.e. the sensing targets (substrates) changes the surface charges on the gate region and the behavior of the gate. When analytes accumulate on the gate area, the net charge on the HEMT surface is changed. The net surface charge alters the 2DEG concentration. This electrical detection technique is simple, fast, and convenient. The detecting signal from the gate is amplified through the drain-source current, making the sensor very sensitive. The electric signal can be easily quantified, recorded and transmit, unlike a fluorescence detection method that needs human inspection and is difficult to be precisely quantify and transmit.

HEMTs can operate over a broad range of temperatures and form the basis of next-generation microwave communication systems. Accordingly, embodiments of the present invention can be implemented as an integrated sensor/wireless chip.

Embodiments utilizing the HEMT sensor can provide a fast response time. In a further embodiment, the subject device can be used as a wireless based sensor to send testing results to a display or separate device.

Biologically modified field effect transistors (bioFETs), either at conventional or nano-dimensions, can directly detect biochemical interactions in aqueous solutions for a wide variety of biosensing applications. To enhance the practicality of bioFETs, a device according to embodiments of the invention is sensitive to biochemical interactions on its surface that is functionalized to probe specific biochemical interactions. In one embodiment, the device is stable in aqueous solutions across a range of pH and salt concentrations. In other embodiments, the gate region of the device is covered with biological probes, which are used as receptor sites for molecules of interest. The conductance of the device changes as reaction occurs between these probes and appropriate species in solution.

In some embodiments, sensors comprise chemical adsorbates on HEMTs where detection originates from compensating or inducing charges at the AlGaN/GaN interface (or AlGaAs/GaAs interface, InGaP/GaAs interface, InAlAs/InGaAs interface, or other HEMT interface) due to the polar molecules in the liquids bonded to the HEMT surface. In certain embodiments, the device is functionalized at the surface of the gate region by different specialized chemicals.

According to an embodiment of the invention, thioglycolic acid can be used to assist in functionalizing an HEMT sensor. For example, a self-assembled monolayer of thioglycolic acid can be adsorbed onto a gold (Au) coated gate region due to interaction between gold and the thiol-group. Following placement of the thioglycolic acid on the sensor surface, specific functionality of interest may be conjugated to the surface, where functionality acts as a receptor for a substrate to be sensed.

According to embodiments of the invention, a sensor can include a synthetic or natural compound as a receptor with the ability to associate with a desired target molecule (substrate) that can be a biomarker. Such receptors include naturally occurring and/or synthetic compounds that display high specificity and sensitivity to a substrate that is one or more target chemicals and/or biological molecules of interest. Suitable compounds include, but are not limited to, antibodies, enzymes, proteins, and aptamers which can associate with a biomarker. The term "biomarker" refers to a biochemical in the body with a particular molecular trait that makes it useful for diagnosing a condition, disorder, or disease and for measuring or indicating the effects or progress of a condition, disorder, or disease. Antibodies are protein molecules that are composed of equal numbers of heavy and light polypeptide amino acid chains held together with disulfide bonds. These highly specialized proteins are able to recognize and bind selectively certain types of antigen molecules at receptor sites. In embodiments of the invention, a sensor employs antibodies to detect specific antigens.

In an embodiment of the invention, the chemistry of the system occurs along a conductive layer, for example, a gold, other metal layer or conductive polymer layer. The conductive layer support the propagation of a high frequency test signal and are capable of binding the substrate (i.e., target), which is a desired antigen or other analyte.

Figure 1:
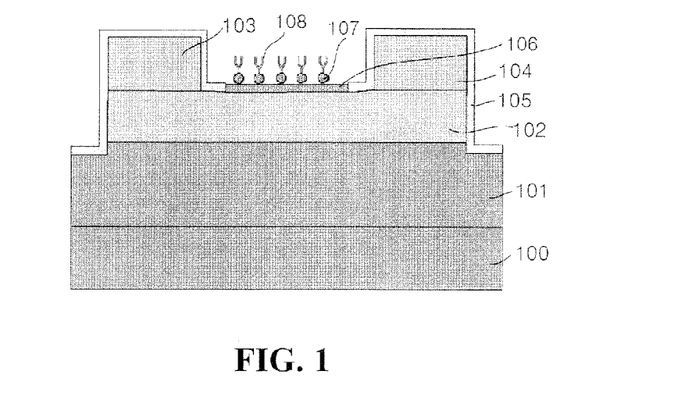
FIG. 1 shows a schematic cross-sectional view of a HEMT based sensor of the invention for cancer detection in accordance with an embodiment of the invention.

A functionalized HEMT capable of cancer detection is shown in FIG. 1. Referring to FIG. 1, an HEMT having a dual layer structure (second material layer 102/first material layer 101) can be provided on a handle substrate 100 (the term substrate in this context is as understood in the electrical arts). Source/Drain electrodes 103 and 104 can be disposed on the surface of the second material layer 102; and a protective film 105 can be disposed on the device while exposing the gate region. For the AlGaAs/GaAs HEMT, first layer 101 is GaAs and second layer 102 is AlGaAs; for the InGaP/GaAs HEMT, first layer 101 is GaAs and second layer 102 is InGaP; and for the InAlAs/InGaAs HEMT, first layer 101 is InGaAs and second layer 102 is InAlAs. In further embodiments, the first layer and the second layer can be arranged in accordance with other III-IV based HEMTs such as AlGaAs/InGaAs PHEMTs, InAlAs/InGaAs PHEMTs, Sb based HEMTs, and InAs based HEMTs. The conductive layer 106 is disposed on the gate region of the HEMT. The conductive layer 106 can be gold.

Since the surface of AlGaN of an AlGaN/GaN HEMT is extremely inert and difficult to oxidize, a thin layer of gold of about 5 nm can be used as an intermediate layer (here, conductive layer 106) between AlGaN and the bio-markers used in embodiments of the invention. The thin layer of gold can also be used as the conductive layer on the surface of the AlGaAs/GaAs HEMT, InGaP/GaAs HEMT, and InAlAs/InGaAs HEMT.

In one embodiment, a binder 107 such as thioglycolic acid bonds the Au layer 106 to antibodies 108 for cancer antigens including, but not limited to, prostate cancer antibodies and breast cancer antigen antibodies such as EGF, c-erbB-2 and CA15-3, in saliva, where the thiogylcolic acid forms a self-assembled monolayer on the gold surfaces. Upon binding of the immobilized antibody to an antigen, the gate potential of the HEMTs changes, resulting in a current change in the HEMT at fixed bias voltage. This change allows quantification of the amount of the target, for example a cancer biomarker, in the solution.

A molecule containing a thiol group can be immobilized on the Au surface by a Au—S bond. Another functional group can be used that is capable of binding with a biomarker; such functional group can be alcohol, aldehyde, carboxylic acid, phosphate or amine groups, for example.

For a breast cancer detector, the immobilized, bio-markers can bind with breast cancer cells. For example, a saliva based breast cancer detector is functionalized in the gate region with chemicals that can bind commercially available breast cancer markers. The gate region of the HEMT can be of a few nanometers to a few millimeters in size. An array of the HEMT sensors can be fabricated on a single chip. Each HEMT can be functionalized with a different cancer marker. The sensing thereby consists of a set of testing results from a series of different bio-markers. Simultaneous breast cancer detections with different bio-markers can increase the accuracy of the cancer detection.

Figure 2A:
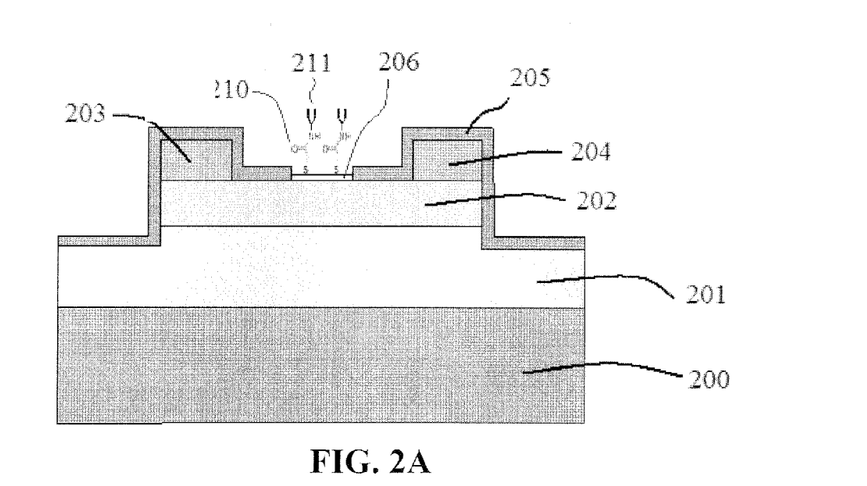
FIG. 2A shows a schematic cross-sectional view of a HEMT based sensor of the invention for prostate cancer detection in accordance with an embodiment of the invention.
Figure 2B:
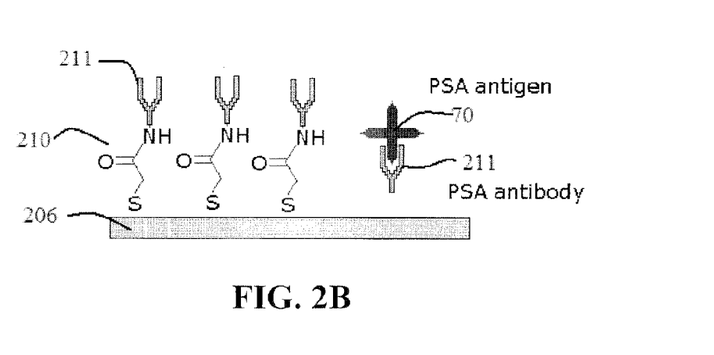
FIG. 2B shows a schematic of a gate area of the HEMI of FIG. 2A functionalized with PSA antibody on thioglycolic acid.

For a prostate cancer detector, bio-markers, immobilized on a gate region of a HEMT, can bind with prostate specific antigen (PSA). Referring to FIGS. 2A and 2B, according to a specific embodiment, PSA can be detected using a functionalized HEMT. The PSA can be specifically recognized through PSA antibody, anchored to the gate area in the form of carboxylate succinimdyl ester.

As shown in FIG. 2A, an HEMT having the dual layer structure (second material layer 202/first material layer 201) can be provided on a handle substrate 200. Source/Drain electrodes 203 and 204 can be disposed on the surface of the second material layer 202; and a protective film 105 can be disposed on the device while exposing the gate region. For the AlGaAs/GaAs HEMT, first layer 201 is GaAs and second layer 202 is AlGaAs; for the InGaP/GaAs HEMT, first layer 201 is GaAs and second layer 202 is InGaP; and for the InAlAs/InGaAs HEMT, first layer 201 is InGaAs and second layer 202 is InAlAs. In further embodiments, the first layer and the second layer can be arranged in accordance with other III-IV based HEMTs such as AlGaAs/InGaAs PHEMTs, InAlAs/InGaAs PHEMTs, Sb based HEMTs, and InAs based HEMTs. A conductive layer 206 is disposed on the gate region of the HEMT. The conductive layer 206 can be gold. A binder 210 bonds the Au layer 206 to PSA antibodies 211 for PSA antigens 70 (see FIG. 2B).

Though the functional group in FIGS. 2A and 2B is shown as a thiol group, embodiments are not limited thereto. Other functional groups capable of binding with a biomarker or antibody can be used.

In an example embodiment using a gold-gated AlGaN/GaN HEMT, the HEMT structure can include a 3 μm thick undoped GaN buffer, a 30 Å thick $Al_{0.3}Ga_{0.7}N$ spacer, and a 220 Å thick Si-doped $Al_{0.3}Ga_{0.7}N$ cap layer, all deposited on a handle substrate. For example, a sapphire substrate can be use used as the handle substrate, but embodiments are not limited thereto. The Au surface can be functionalized with a specific bifunctional molecule. The thioglycolic acid, $HSCH_2COOH$, can be used attached to the Au surface in the gate area, as a self assembled monolayer adsorbed on the gold gate.

The binding of the thioglycolic acid to the Au surface in the gate area can be performed such that the COOH groups are available for further chemical functionalization. The carboxylic acid functional groups can be activated to form succinimidyl ester groups on the gate area of the HEMT, as shown in the detail of FIG. 2B. The device can be incubated in a phosphate buffered saline (PBS) solution of anti-PSA monoclonal antibody to allow for attachment of the PSA antibody 211.

As previously described, the electrons in the two-dimensional electron gas (2DEG) channel of the HEMT are induced by piezoelectric and spontaneous polarization effects. This 2DEG is located at the interface between the first material layer 201 (e.g., GaN layer) and the second material layer 202 (e.g., AlGaN layer). There are positive counter charges at the AlGaN surface layer induced by the 2DEG. Any slight changes in the ambient of the HEMT affect the surface charges of the HEMT. These changes in the surface charge are transduced into a change in the concentration of the 2DEG in the HEMTs, leading to the slight decrease in the conductance for the device after PSA incubation.

Accordingly, the electronic detection of biomolecules can occur with a compact sensor chip, which can be integrated with a commercial available hand-held wireless transmitter to realize a portable, fast and high sensitivity prostate cancer detector.

One implementation of the invention is a portable or hand-held saliva based cancer sensor. Other embodiments of the invention are sensor to analyze other bodily fluids or excretions such as breath, urine or blood. Advantages of the sensors include fast response time for results, portability and low cost. In one embodiment, a chemical sensor array can be integrated with wireless communication circuits for remote sensor applications. For example, a digital signal cancer detector can wirelessly send the testing results directly to a user's doctor.

Figure 3A:
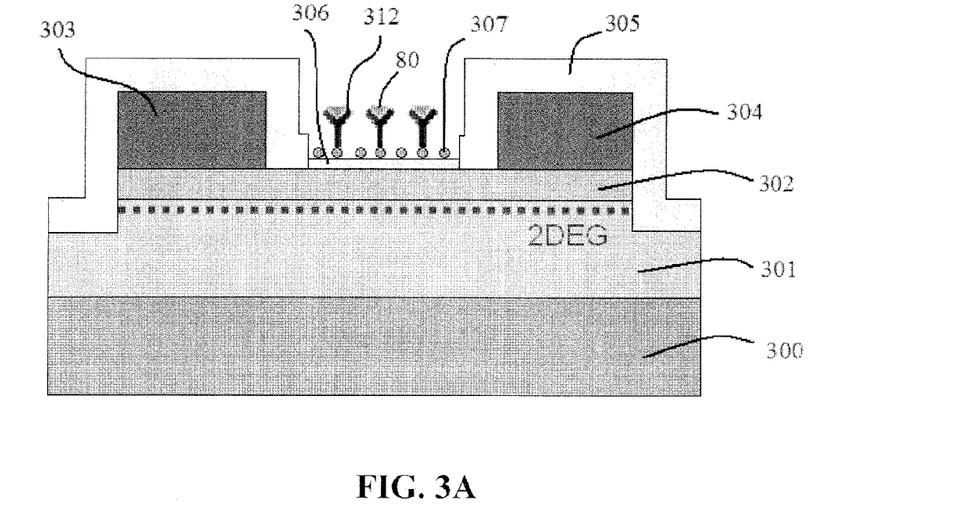
FIG. 3A shows a schematic cross-sectional view of a HEMT based sensor of the invention for kidney injury detection in accordance with an embodiment of the invention.
Figure 3B:
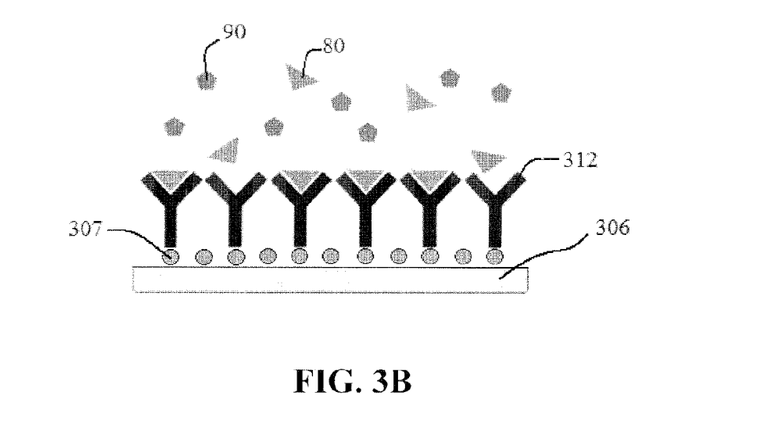
FIG. 3B shows a schematic of a gate area of the HEMT of FIG. 3A functionalized with KIM-1 antibody on thioglycolic acid.

According to another embodiment, the subject sensor can be used to quantify the amount of kidney injury molecule-1 (KIM-1) biomarker present in a solution. Referring to FIGS. 3A and 3B, according to a specific embodiment, KIM-1 biomarker can be detected using a functionalized HEMT. The KIM-1 can be specifically recognized through KIM-1 antibodies that are anchored to a gold surface on the gate region of the HEMT with thioglycolic acid. When in the presence of KIM-1, the gate potential of the HEMTs changes, resulting in a current change in the HEMT at fixed bias voltage. This change can be used to quantify the amount of the KIM-1 biomarker present in the solution.

As shown in FIG. 3A, an HEMT having the dual layer structure (second material layer 302/first material layer 301) can be provided on a handle substrate 300. Source/Drain electrodes 303 and 304 can be disposed on the surface of the second material layer 302; and a protective film 305 can be disposed on the device while exposing the gate region. For the AlGaAs/GaAs HEMT, first layer 301 is GaAs and second layer 302 is AlGaAs; for the InGaP/GaAs HEMT, first layer 301 is GaAs and second layer 302 is InGaP; and for the InAlAs/InGaAs HEMT, first layer 301 is InGaAs and second layer 302 is InAlAs. In further embodiments, the first layer and the second layer can be arranged in accordance with other III-IV based HEMTs such as AlGaAs/InGaAs PHEMTs, InAlAs/InGaAs PHEMTs, Sb based HEMTs, and InAs based HEMTs. A conductive layer 306 is disposed on the gate region of the HEMT. The conductive layer 306 can be gold. A binder 307 bonds the Au layer 306 to KIM-1 antibodies 312 for KIM-1 biomarkers 80.

As illustrated in FIG. 3B, the KIM-1 antibodies 312 are selective to KIM-1 biomarkers 80, and do not attach other molecules 90 that are in the solution.

In an example embodiment using a gold-gated AlGaN/GaN HEMT, the HEMT structure can include a 2 μm thick undoped GaN buffer and 250 Å thick undoped $Al_{0.25}Ga_{0.75}N$ cap layer, all deposited on a handle substrate. For example, a silicon substrate can be used as the handle substrate, but embodiments are not limited thereto. The Au surface can be functionalized with a self-assembled monolayer of thioglycolic acid. The protective layer 305 can be, for example, poly(methyl methacrylate) (PMMA).

The KIM-1 antibody can be immobilized on the HEMT through the reaction between carboxyl group on thioglycolic acid and amine group on KIM-1 antibody. Through the selective binding of KIM-1 with antibody, there are charges accumulated at the surface, and these surface charges are transduced into a change in the carrier concentration of AlGaN/GaN 2DEG, leading to a decrease in the conductance of the device after KIM-1 exposure.

HEMTs are compatible with AKI biomarker, KIM-1, and can be useful for preclinical and clinical applications. Similar surface modifications can be applied for detecting other important disease biomarkers and a compact disease diagnosis array can be realized for multiplex disease analysis.

In yet another embodiment, gateless HEMT structures can distinguish liquids with different polarities and can quantitatively measure pH over a broad range. The sensing mechanism for chemical adsorbates in piezoelectric materials originates from compensation of the polarization induced bound surface charge by interaction with the polar molecules in liquids. In gateless aluminum gallium nitride/gallium nitride (AlGaN/GaN) heterostructure transistors, the native oxide on the nitride surface is responsible for the pH sensitivity of the response to electrolyte solutions.

Figure 4:
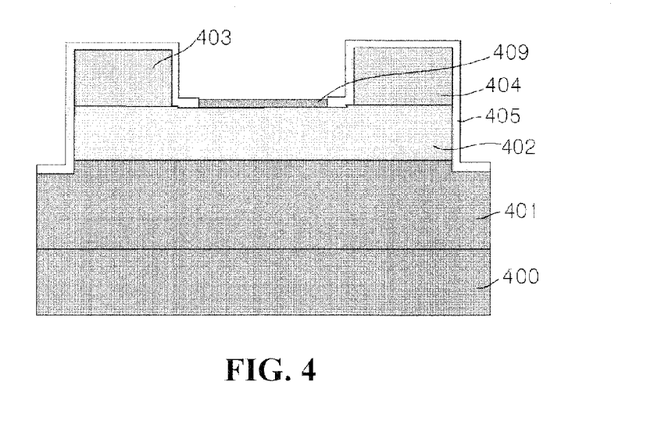
FIG. 4 shows a schematic cross-sectional view of a HEMT based sensor of the invention for pH detection in accordance with an embodiment of the invention.

Referring to FIG. 4, according to embodiments of the present invention, a gate dielectric layer 409 is included on the gate region of a HEMT. The gate dielectric layer can be a thin non-native metal oxide, for example $Sc_2O_3$. The gate dielectric layer can provide more sensitive and reproducible hydronium ion, $H_3O^+$ (pH) sensing. Usually, it is difficult to control the compositions and thickness of native oxides. For embodiments of the invention, a metal oxide such as $Sc_2O_3$ can be grown by a molecule beam epitaxy system with excellent composition and thickness control. Other gate dielectric layers, such as metal nitrides, can be used rather than metal oxide dielectric layers. According to certain embodiments, the oxide deposition methods can include, but are not limited to, plasma enhanced chemical vapor deposition, thermally grown native oxide, chemical vapor deposition, atomic layer deposition, dc or rf sputtering and laser ablation. The pH response of oxide/nitride interface can be modeled in terms of formation of hydroxyl groups that lead to a hydronium ion concentration (pH) dependent net surface change with a resulting change in voltage drop at the semiconductor/liquid interface.

Another embodiment of the invention is a pH meter for fluids such as breath, saliva, urine or blood. Gates can be functionalized with noble metal oxides for detecting proton and hydroxide ions (hydronium ions). In one embodiment, a $Sc_2O_3$ gate dielectric is placed on HEMTs to provide high sensitivity for detecting changes in pH of electrolyte solutions. The HEMTs can be used to monitor solution pH changes between 7 and 8, a range of interest for testing human blood.

As shown in FIG. 4, an HEMT having the dual layer structure (second material layer 402/first material layer 401) can be provided on a handle substrate 400. Source/Drain electrodes 403 and 404 can be disposed on the surface of the second material layer 402; and a protective film 405 can be disposed on the device while exposing the gate region. For the AlGaAs/GaAs HEMT, first layer 401 is GaAs and second layer 402 is AlGaAs; for the InGaP/GaAs HEMT, first layer 401 is GaAs and second layer 402 is InGaP; and for the InAlAs/InGaAs HEMT, first layer 401 is InGaAs and second layer 402 is InAlAs. In further embodiments, the first layer and the second layer can be arranged in accordance with other III-IV based HEMTs such as AlGaAs/InGaAs PHEMTs, InAlAs/InGaAs PHEMTs, Sb based HEMTs, and InAs based HEMTs. A gate dielectric layer 409 is disposed on the gate region of the HEMT to provide additional sensitivity to pH.

In an example embodiment using an AlGaN/GaN HEMT, the HEMT structure can include a 2 µm thick undoped GaN buffer and 250 Å thick undoped $Al_{0.25}Ga_{0.75}N$ cap layer, all deposited on a handle substrate. For example, a silicon substrate can be used as the handle substrate but embodiments are not limited thereto. A 100 Å $Sc_2O_3$ layer can be deposited as a gate dielectric through a contact window The adsorption of aqueous solution of different pH on the surface of the HEMT affects the surface potential and device characteristics. The current significantly increases as the pH is decreased upon exposure to these aqueous solutions. The HEMT sensor with $Sc_2O_3$ gate dielectric can be used to differentiate between liquids into which a small amount of leakage of another substance has occurred. The electrons in the two-dimensional electron gas (2DEG) channel of the AlGaN/GaN HEMT are induced by piezoelectric and spontaneous polarization effects. This 2DEG is located at the interface between the GaN layer and AlGaN layer. There are positive counter charges at the AlGaN surface layer induced by the 2DEG. Any change in the ambient of the AlGaN/GaN HEMT affects the surface charges of the device. These changes in the surface charge are transduced into a change in the concentration of the 2DEG. Different pH exhibit different degrees of interaction with the HEMT surface.

According to an embodiment of the subject invention, real-time detection of the pH of exhaled breath uses a breathing tube and ice bath with a HEMT. The breathing tube samples exhaled breath and the ice bath condenses the sample that is applied to the HEMT.

Figure 5A:
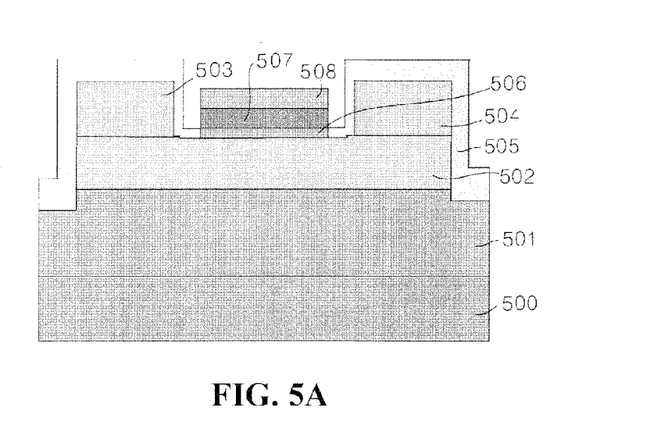
FIG. 5A shows a schematic cross sectional view of a Ag/AgCl gated HEMT for chloride detection according to an embodiment of the invention.

In another embodiment, a chloride detector can be provided. Referring to FIG. 5A, a chloride sensor can include an HEMT formed on a handle substrate 500. An electrode can be formed on the gate region of the HEMT. The electrode can include a titanium (Ti) thin film 506 and a silver (Ag) thin film 507. Then, a chloride selective film 508 can be provided on the electrode. The chloride selective film can be silver chloride (AgCl). By forming the silver thin film for the electrode, the silver chloride can be formed through selective area potentiostatic anodization. The HEMT can be an AlGaN/GaN HEMT formed as a GaN layer 501 and an AlGaN layer 502 on the handle substrate 500. A source electrode 503 and a drain electrode 504 can be disposed on the AlGaN layer 502. In other embodiments, the HEMT can be an AlGaAs/GaAs HEMT, InGaP/GaAs HEMT, or InAlAs/InGaAs HEMT. In further embodiments, the HEMT can be an AlGaAs/InGaAs PHEMT, InAlAs/InGaAs PHEMT, Sb based HEMT, or InAs based HEMT. In a further embodiment, a passivation layer 505 can be provided to encapsulate the source and drain regions 503 and 504.

An HEMT with a Ag/AgCl gate can exhibit significant changes in channel conductance upon exposing the gate region to various concentrations of chloride ion solutions. The Ag/AgCl gate electrode changes electrical potential when it encounters chlorine ions. This gate potential changes lead to a change of surface charge in the gate region of the HEMT, inducing a higher positive charge on the AlGaN 502 surface, and increasing the piezo-induced charge density in the HEMT channel. These anions create an image positive charge on the Ag gate metal 507/508 for the required neutrality, thus increasing the drain current of the HEMT. Embodiments of the present invention can use these behaviors to provide a chloride sensing device.

Figure 5B:
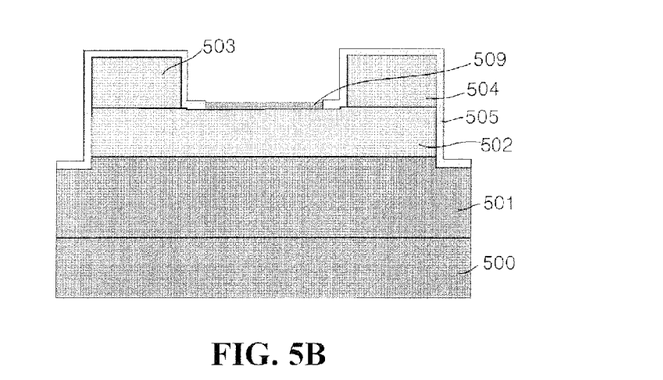
FIG. 5B shows a schematic cross sectional view of an InN gated HEMT for chloride detection according to an embodiment of the invention.

Referring to FIG. 5B, according to another embodiment, a chloride sensor can include an HEMT formed on a substrate 500. A chlorine selective film 509 can be provided on the gate region of the HEMT. The HEMT can be an AlGaN/GaN HEMT formed as a GaN layer 501 and an AlGaN layer 502 on the handle substrate 500. In other embodiments, the HEMT can be an AlGaAs/GaAs HEMT, InGaP/GaAs HEMT, or InAlAs/InGaAs HEMT. In further embodiments, the HEMT can be an AlGaAs/InGaAs PHEMT, InAlAs/InGaAs PHEMT, Sb based HEMT, or InAs based HEMT. A source electrode 503 and a drain electrode 504 can be disposed on the AlGaN layer 102. In a further embodiment, a passivation layer 505 can be provided to encapsulate the source and drain regions 503 and 504. According to an embodiment, an indium nitride (InN) layer 509 can be epitaxially grown on the surface of the AlGaN layer 502 in the gate area of the HEMT. The positively charged surface donor states of the InN layer allow negatively charged chlorine ions to be selectively attracted to the InN surface. The presence of chlorine creates a potentiometric response from the InN layer, which in turn affects the current of the HEMT.

In one embodiment, the InN layer can be grown on the AlGaN surface using a molecular-beam epitaxy system equipped with a radio frequency (RF) nitrogen plasma source or metal organic chemical vapor deposition system on the surface of the AlGaN layer in the gate region of the HEMT.

Embodiments of the subject sensors can be used to measure chloride ion concentration in water. In addition, embodiments of the subject sensors can be used for measurement of analytes and other bio-sensing applications.

In an embodiment, the subject chlorine sensor can be recycled. For example, the chlorine sensor can be used for multiple chlorine tests by performing a resetting operation. The resetting operation can be a de-ionized (DI) water rinse.

In another embodiment of the invention, a sensor is provided that can be used to detect heavy metals. Heavy metal detection involves selecting a powerful receptor and densely coating it on the surface of HEMTs. $Hg^{2+}$, $Cu^{+2}$ and $Pb^{2+}$ detection is based on an effective medical approach for heavy metal poisoning, so called "Chelation Therapy." In one embodiment, chelating agents remove heavy metal ions from a sample, where chelating ligands and metal ions bind to form metal complexes, normally called "chelation." A strong chelating agent is dimercaprol (BAL), which contains two thiol groups capable of reacting with arsenic, lead and mercury. Other widely used chelating agents include diaminoethanetetraacetic acid (EDTA), 2,3-bis-sulfanylbutanedioic acid (DMSA), and 2,3-dimercapto-1-propanesulfonic acid (DMPS.

Figure 6A:
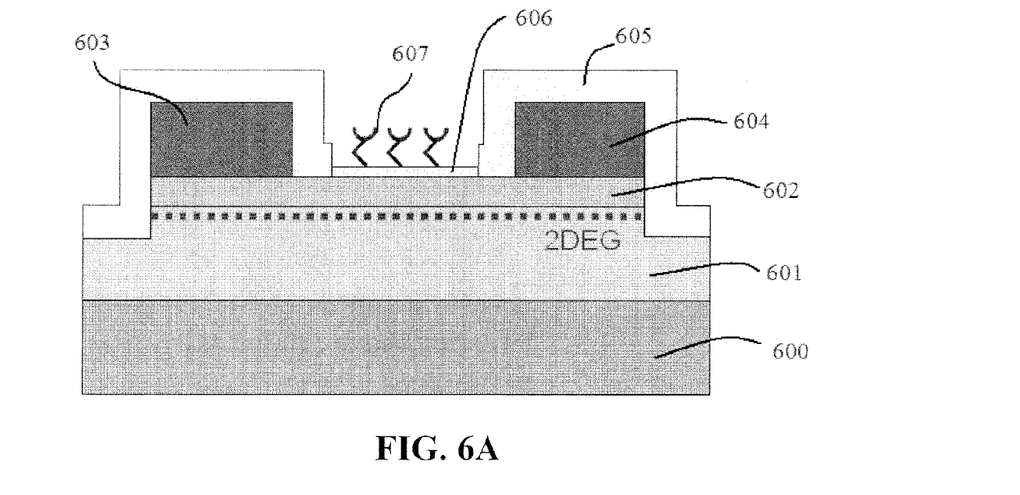
FIG. 6A shows a schematic cross-sectional view of a HEMT based sensor of the invention for heavy metal detection in accordance with an embodiment of the invention.

In one embodiment of the invention, $Hg^{2+}$, $Cu^{+2}$ or $Pb^{2+}$ is detected when chelating receptors immobilize the metal on the HEMT surface. Referring to FIG. 6A, an HEMT having the dual layer structure (second material layer 602/first material layer 601) can be provided on a handle substrate 600. Source/Drain electrodes 603 and 604 can be disposed on the surface of the second material layer 602; and a protective film 605 can be disposed on the device while exposing the gate region. For the AlGaAs/GaAs HEMT, first layer 601 is GaAs and second layer 602 is AlGaAs; for the InGaP/GaAs HEMT, first layer 601 is GaAs and second layer 602 is InGaP; and for the InAlAs/InGaAs HEMT, first layer 601 is InGaAs and second layer 602 is InAlAs. In further embodiments, the first layer and the second layer can be arranged in accordance with other III-IV based HEMTs such as AlGaAs/InGaAs PHEMTs, InAlAs/InGaAs PHEMTs, Sb based HEMTs, and InAs based HEMTs. A conductive layer 606 is disposed on the gate region of the HEMT. The conductive layer 606 can be gold. A chelating receptor 607 can be bonded to the Au layer 606. Gold permits deposition of any chelating agent comprising a thiol group, on the surface through Au—S bonding. The thiol, amine, and carboxyl groups of the bound chelating agents bind heavy metal ions to the surface of the HEMT. In a specific embodiment, the functionalization is an Au-coated gate area with thioglycolic acid, $HSCH_2COOH$, for Hg(II) detection. A self assembled monolayer of thioglycolic acid molecules is adsorbed onto the gold gate by a S—Au bond between the gold surface and thiol-group. The immobilized carboxyl groups function as receptors to capture $Hg^{2+}$, $Cu^{+2}$ or $Pb^{2+}$ ions. Alternative binding groups are derived from cysteamine ($NH_2CH_2CH_2SH$) or 1,2-ethanedithiol ($HSCH_2CH_2SH$), for example.

Figure 6B:
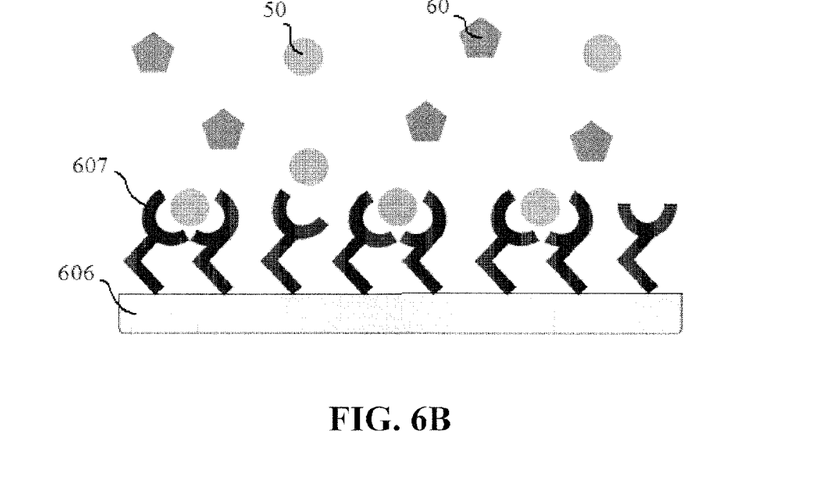
FIG. 6B shows a schematic of a gate area of the HEMT of FIG. 6A functionalized with a chelating agent.

As illustrated in FIG. 6B, the chelating receptors 607 are selective to a particular heavy metal 50, and do riot attach other metal ions 60 that are in the solution. In one embodiment, the gold-gated region 606 is functionalized with chelating receptors 607 immobilized on the HEMT surface, such as BAL, EDTA, DMSA, and DMPS. One portion of the chelating agent binds to the Au surface and the other portions chelates with heavy metals 50, such as $Hg^{2+}$, $Cu^{+2}$ or $Pb^{2+}$. The charge of the metal ions affects the gate potential of HEMTs. The change in current in the HEMT at fixed bias voltage allows quantification of the amount of the heavy metal ions in a solution. In one embodiment, the device is a portable or hand-held trace heavy-metal sensor for environmental and health related applications. The sensor can detect heavy metals in aqueous solution including breath condensate, urine or blood. Advantages of the sensing device include fast response time, portability and low cost. In one embodiment, a heavy metal detector can be used as a wireless based sensor to transmit a digital signal of the test results directly to a recipient.

$Hg^{2+}$ and $Cu^{2+}$ ions are easily detected with sensors fabricated with Au-gated and thioglycolic acid functionalized Au-gated HEMTs.

In an example embodiment, using an AlGaN/GaN HEMT, the HEMT structure can include a 2 μm thick undoped GaN buffer and 250 Å thick undoped $Al_{0.25}Ga_{0.75}N$ cap layer, all deposited on a handle substrate. The handle substrate can be, for example, a sapphire substrate. Two (or more) types of sensors can be established. One sensor can have a bare Au-gate and another sensor can have an Au-gate functionalized with a self-assembled monolayer of thioglycolic acid. A 500-nm-thick poly(methyl methacrylate) (PMMA) film, other polymer layer or dielectric layer can be used as a protective layer 605 to encapsulate the source/drain regions, with only the gate region exposed to allow the liquid solutions to access the bare Au-gate or functionalized Au-gate surface.

For the thioglycolic acid functionalized AlGaN/GaN HEMT, the thioglycolic acid molecules on the Au surface align with carboxylic acid functional group extending toward the solution. The carboxylic acid functional group of the adjacent thioglycolic acid molecules can form chelates (R—COO$^-$(Hg$^{2+}$)$^-$OOC—R) with the $Hg^{2+}$ ions. Upon chelation, one would expect the charges of trapped $Hg^{2+}$ ion in the R—COO$^-$(Hg$^{2+}$)$^-$OOC—R to change the polarity of the thioglycolic acid molecules. Because $Hg^{2+}$ ions were used in the experiments, no Au-mercury amalgam is expected to form on the bare Au-surface.

The difference in the response between the bare Au-gate and the thioglycolic acid functionalized sensor offers the possibility for selective detection for $Hg^{2+}$ and $Cu^{2+}$ ions presented in a single solution with a sensor chip containing both type of sensors. The fabrication of both sensors can be substantially identical except for the thioglycolic acid functionalized sensor, which has an additional functionalization step. This step can be accomplished with micro-inkjet system to locally functionalize surfaces. The bare Au-gate and thioglycolic acid functionalized sensors also showed excellent sensing selectivity (over 100 times higher selectivity) over $Na^+$ and $Mg^{2+}$ ions.

Most semiconductor based chemical sensors are not reusable. The bare Au-gate and thioglycolic acid functionalized sensors showed very good reusability.

The sensor can be integrated with a commercial available hand-held wireless transmitter to realize a portable, fast response and high sensitivity $Hg^{2+}$ and $Cu^{2-}$ ion detector.

In summary, bared Au-gate and thioglycolic acid functionalized. AlGaN/GaN HEMT sensors have demonstrable ability to detect heavy ions. The bare Au-gate sensor was sensitive to $Hg^{2+}$ and thioglycolic acid functionalized sensors could detect both $Hg^{2+}$ and $Cu^+$ ions. By fabricating an array of the sensors on a single chip and selectively functionalizing some sensors with thioglycolic acid, a multi-functional specific detector can be fabricated. Such a sensor array can be used to detect quantitatively $Hg^{2+}$ ions in $Cu^{2-}$ ion solution or $Cu^{2-}$ ions in $Hg^{2+}$ ion solution. Both bare Au-gate and thioglycolic acid functionalized sensor can be repeatedly used after a simple DI water rinse.

In other embodiments of the invention, a nanorod gated HEMT is used as a detector for glucose. The nanorod arrays can be selectively grown on the gate area to immobilize glucose oxidase (GOx). The nanorods can be, for example, metal oxide and nitride based nanorods. Nanorod metal oxides include, but are not limited to, SnO, $TiO_2$, GaN, MgO, ZnMgO, and $In_2O_3$ nanorods. For example, one-dimensional ZnO nanorods on the gate area result in a very high specific surface area with high surface to volume ratio and provide favorable micro-environments for the immobilization of GOx.

Figure 7:
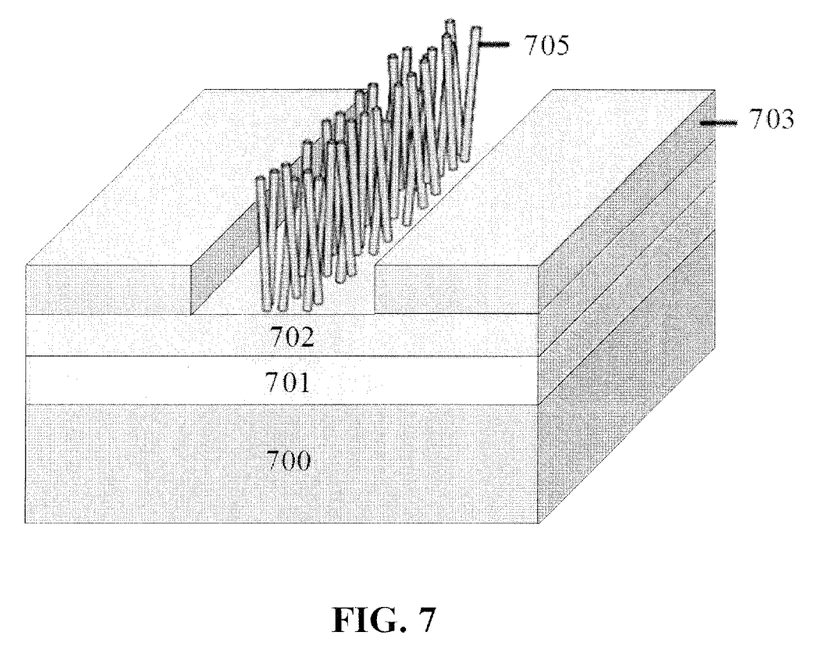
FIG. 7 shows a schematic perspective view of a ZnO nanorod gated HEMT in accordance with an embodiment of the present invention.

As shown in FIG. 7, an HEMT having the dual layer structure (second material layer 702/first material layer 701) can be provided on a handle substrate 700. Source/Drain electrodes 703 can be disposed on the surface of the second material layer 702. For the AlGaAs/GaAs HEMT, first layer 701 is GaAs and second layer 702 is AlGaAs; for the InGaP/GaAs HEMT, first layer 701 is GaAs and second layer 702 is InGaP; and for the InAlAs/InGaAs HEMT, first layer 701 is InGaAs and second layer 702 is InAlAs. In further embodiments, the first layer and the second layer can be arranged in accordance with other III-IV based HEMTs such as AlGaAs/InGaAs PHEMTs, InAlAs/InGaAs PHEMTs, Sb based HEMTs, and InAs based HEMTs. Nanorods 705 are disposed on the gate region of the HEMT to provide sensitivity to glucose.

In an example embodiment using an AlGaN/GaN HEW, the HEMT structure can include a 3 μm thick undoped GaN buffer, 30 Å thick $Al_{0.3}Ga_{0.7}N$ spacer, 220 Å thick Si-doped $Al_{0.3}Ga_{0.7}N$ cap layer, all deposited on a handle substrate. The handle substrate can be, for example, a sapphire substrate or silicon carbide, but embodiments are not limited thereto. For example, a silicon substrate may be used. Nanorods, such as ZnO nanorods, carbon nanotubes, $TiO_2$ nanorods, or other nano-oxide particles, can be grown on the HEMT substrate. The ZnO nanoparticle size is dependent on the nanocrystal seed preparation time, which in turn, controls the diameters of the ZnO nanorods Here, sensitivity is increases while maintaining gate dimension by growing 3D structures on the gate sensing area to increase the total sensing area with the area expansion to the third dimension.

The ZnO nanorods matrix provides a microenvironment for immobilizing negatively charged GOx and retains its bioactivity, and passes charges produce during the GOx and glucose interaction to the HEMT.

Because of the fast response time and low volume of the exhaled breath condensate (EBC) required, a handheld real-time glucose sensor can be made.

All patents, patent applications, provisional applications, and publications referred to or cited herein are incorporated by reference in their entirety, including all Figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

What is claimed is:

1. A high electron mobility transistor (HEMT) based sensor comprising:
   a HEMT having a source, a drain, and a gate area
   at least one target receptor on the gate region of the HEMT, the at least one target receptor functionalizing the HEMT as a sensor for a target corresponding to the at least one target receptor,
   wherein the source of the HEMT is configured to receive a fixed voltage and an output current resulting from exposure of the at least one target receptor to an amount of the target is sensed at the drain of the HEMT; and
   wherein the HEMT is an AlGaAs/GaAs HEMT, an InGaP/GaAs HEMT, an InAlAs/InGaAs HEMT, an AlGaAs/InGaAs PHEMT, an InAlAs/InGaAs PHEMT, an Sb based HEMT, or an InAs based HEMT.

2. The HEMT based sensor according to claim 1, wherein the at least one target receptor comprises a cancer antigen antibody.

3. The HEMT based sensor according to claim 2, wherein the cancer antigen antibody is a prostate specific antigen (PSA) or one or more breast cancer antigen antibodies selected from the group consisting of EGF, c-erbB-2, and CA15-3.

4. The HEMT based sensor according to claim 2, wherein the functionalization further comprises a gold layer on the gate region of the HEMT; and a binding group layer coupling the cancer antigen antibody to the gold layer.

5. The HEMT based sensor according to claim 4, wherein the binding group layer comprises thioglycolic acid.

6. The HEMT based sensor according to claim 1, wherein the at least one target receptor comprises a kidney injury molecule-1 (KIM-1) antibody.

7. The HEMT based sensor according to claim 6, wherein the functionalization further comprises a gold layer on the gate region of the HEMT; and a binding group layer coupling the KIM-1 antibody to the gold layer.

8. The HEMT based sensor according to claim 7, wherein the binding group layer comprises thioglycolic acid.

9. The HEMT based sensor according to claim 1, wherein the at least one target receptor comprises a gate dielectric capable of sensitivity to hydronium ions, the gate dielectric formed on the gate region of the HEMT.

10. The HEMT based sensor according to claim 9, wherein the gate dielectric comprises Sc2O3, Al2O3, TiO2, MgO, In2O3, SnO2, ZnO, or ZnMgO.

11. The HEMT based sensor according to claim 1, wherein the at least one target receptor comprises metal chloride.

12. The HEMT based sensor according to claim 11, wherein the metal chloride comprises silver-chloride.

13. The HEMT based sensor according to claim 12, wherein the functionalization further comprises a titanium thin film electrode on the gate region of the HEMT and a silver thin film on the titanium thin film, wherein the silver-chloride is provided on the silver thin film through potentiostatic anodization.

14. The HEMT based sensor according to claim 1, wherein the at least one target receptor comprises indium nitride.

15. The HEMT based sensor according to claim 1, wherein the at least one target receptor comprises at least one chelating agent for a heavy metal.

16. The HEMT based sensor according to claim 15, wherein the chelating agent comprises thioglycolic acid (HSCH2COOH), cysteamine (NH2CH2CH2SH), 1,2-ethanedithiol (HSCH2CH2SH), dimercaprol (BAL), diaminoethanetetraacetic acid (EDTA), 2,3-bis-sulfanylbutanedioic acid (DMSA), 2,3-dimercapto-1-propanesulfonic acid (DMPS), or any combination thereof.

17. The HEMT based sensor according to claim 1, wherein the functionalization further comprises a gate dielectric layer comprising nanorods and the at least one target receptor comprises glucose oxidase immobilized on the nanorods.

18. The HEMT based sensor according to claim 17, wherein the nanorods comprise a metal oxide.

19. The HEMT based sensor according to claim 18, wherein the metal oxide comprises Sc2O3, Al2O3, TiO2, MgO, In2O3, SnO2, ZnO, or ZnMgO.

* * * * *

UNITED STATES PATENT AND TRADEMARK OFFICE
CERTIFICATE OF CORRECTION

PATENT NO. : 8,835,984 B2  Page 1 of 1
APPLICATION NO. : 12/992002
DATED : September 16, 2014
INVENTOR(S) : Fan Ren et al.

It is certified that error appears in the above-identified patent and that said Letters Patent is hereby corrected as shown below:

In the Specification

Column 1,
Line 17, "tiled Sep. 28," should read --filed September 28,--.

Column 3,
Line 62, "HEMI" should read --HEMT--.

Column 12,
Lines 8-9, "do riot attach other" should read --do not attach to other--.

Column 13,
Line 45, "HEW," should read --HEMT,--.

Signed and Sealed this
Thirty-first Day of March, 2015

Michelle K. Lee
*Director of the United States Patent and Trademark Office*